(12) United States Patent
Tohmeh et al.

(10) Patent No.: US 8,623,088 B1
(45) Date of Patent: Jan. 7, 2014

(54) SPINAL FUSION IMPLANT AND RELATED METHODS

(75) Inventors: Antoine G. Tohmeh, Spokane, WA (US); Joseph Clark, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 132 days.

(21) Appl. No.: 12/329,195

(22) Filed: Dec. 5, 2008

Related U.S. Application Data

(63) Continuation-in-part of application No. 11/488,744, filed on Jul. 17, 2006, now Pat. No. 7,867,277.

(60) Provisional application No. 60/699,597, filed on Jul. 15, 2005.

(51) Int. Cl.
*A61F 2/44* (2006.01)

(52) U.S. Cl.
USPC ...................................................... 623/17.11

(58) Field of Classification Search
USPC .................... 623/17.11–17.16; 606/247–249
See application file for complete search history.

(56) References Cited

U.S. PATENT DOCUMENTS

| | | | |
|---|---|---|---|
| 3,486,505 A | 12/1969 | Morrison | |
| 3,518,993 A | 7/1970 | Blake | |
| 3,604,487 A | 9/1971 | Gilbert | |
| 3,745,995 A | 7/1973 | Kraus | |
| 3,848,601 A | 11/1974 | Ma et al. | |
| 4,026,304 A | 5/1977 | Levy | |
| 4,026,305 A | 5/1977 | Brownlee et al. | |
| 4,349,921 A | * 9/1982 | Kuntz | 623/17.16 |
| 4,646,738 A | 3/1987 | Trott | |
| 4,657,550 A | 4/1987 | Daher | |
| 4,714,469 A | 12/1987 | Kenna | |
| 4,743,256 A | 5/1988 | Brantigan | |

(Continued)

FOREIGN PATENT DOCUMENTS

| | | |
|---|---|---|
| CA | 2015507 | 6/1991 |
| EP | 369603 | 5/1990 |

(Continued)

OTHER PUBLICATIONS

Alleyne et al., "Current and future approaches to lumbar disc surgery: A literature review," Medscape Orthopedics & Sports Medicine, www.medscape.com/Medscape/OrthoSportsMed/1997/v01.n11/.../mos3057), 1997.

(Continued)

*Primary Examiner* — Mary Hoffman
(74) *Attorney, Agent, or Firm* — Jonathan Spangler; Jennifer Russell; Heather Prado

(57) ABSTRACT

A spinal fusion implant of non-bone construction to be introduced into any variety of spinal target sites. The spinal fusion implant of the present invention includes a top surface, a bottom surface, first and second lateral sides, a proximal (posterior) end and a distal (anterior) end. The spinal fusion implant of the present invention may be used to provide temporary or permanent fixation within an orthopedic target site. To do so, the spinal fusion implant may be introduced into a disc space while locked to a surgical insertion instrument and thereafter employed in the proper orientation and released. Once deposited in the disc space, the spinal fusion implant of the present invention effects spinal fusion over time as the natural healing process integrates and binds the implant.

11 Claims, 12 Drawing Sheets

(56) References Cited

U.S. PATENT DOCUMENTS

| | | | |
|---|---|---|---|
| 4,781,591 A | | 11/1988 | Allen |
| 4,834,757 A | * | 5/1989 | Brantigan ............... 623/17.11 |
| 4,863,476 A | | 9/1989 | Shepperd |
| 4,877,020 A | | 10/1989 | Vich |
| 4,878,915 A | | 11/1989 | Brantigan |
| 4,904,261 A | | 2/1990 | Dove et al. |
| 4,932,975 A | | 6/1990 | Main et al. |
| 4,961,740 A | | 10/1990 | Ray et al. |
| 4,962,766 A | | 10/1990 | Herzon |
| 5,026,373 A | | 6/1991 | Ray et al. |
| 5,055,104 A | | 10/1991 | Ray |
| 5,062,845 A | | 11/1991 | Kuslich et al. |
| 5,092,572 A | | 3/1992 | Litwak et al. |
| 5,133,717 A | | 7/1992 | Chopin |
| 5,133,755 A | | 7/1992 | Brekke |
| 5,171,278 A | | 12/1992 | Pisharodi |
| 5,192,327 A | | 3/1993 | Brantigan |
| 5,217,497 A | | 6/1993 | Mehdian |
| 5,269,785 A | | 12/1993 | Bonutti |
| 5,284,153 A | | 2/1994 | Raymond et al. |
| 5,290,494 A | | 3/1994 | Coombes et al. |
| 5,300,076 A | | 4/1994 | Leriche |
| 5,304,210 A | | 4/1994 | Crook |
| 5,306,307 A | | 4/1994 | Senter et al. |
| 5,306,309 A | | 4/1994 | Wagner et al. |
| 5,322,505 A | | 6/1994 | Krause |
| 5,334,205 A | | 8/1994 | Cain |
| 5,336,223 A | | 8/1994 | Rogers |
| 5,339,801 A | | 8/1994 | Poloyko et al. |
| 5,341,707 A | | 8/1994 | Bond |
| 5,364,400 A | | 11/1994 | Rego, Jr. et al. |
| 5,395,372 A | | 3/1995 | Holt et al. |
| 5,397,363 A | | 3/1995 | Gelbard |
| 5,405,391 A | | 4/1995 | Hednerson et al. |
| 5,413,602 A | | 5/1995 | Metz-Stavenhagen |
| 5,425,772 A | * | 6/1995 | Brantigan ............... 623/17.11 |
| 5,431,658 A | | 7/1995 | Moskovich |
| 5,443,514 A | * | 8/1995 | Steffee ..................... 128/898 |
| 5,443,515 A | | 8/1995 | Cohen et al. |
| 5,445,639 A | | 8/1995 | Kuslich et al. |
| 5,454,811 A | | 10/1995 | Huebner |
| 5,458,638 A | | 10/1995 | Kuslich et al. |
| 5,484,403 A | | 1/1996 | Yoakum et al. |
| 5,489,307 A | | 2/1996 | Kuslich et al. |
| 5,489,308 A | | 2/1996 | Kuslich et al. |
| 5,505,732 A | | 4/1996 | Michelson |
| 5,522,879 A | | 6/1996 | Scopelianos |
| 5,522,899 A | | 6/1996 | Michelson |
| 5,524,624 A | | 6/1996 | Tepper et al. |
| 5,527,312 A | | 6/1996 | Ray |
| 5,534,029 A | | 7/1996 | Shima |
| 5,534,030 A | | 7/1996 | Navarro et al. |
| 5,540,688 A | | 7/1996 | Navas |
| 5,545,222 A | | 8/1996 | Bonutti |
| 5,554,191 A | | 9/1996 | Lahille et al. |
| 5,562,736 A | | 10/1996 | Ray et al. |
| 5,565,005 A | | 10/1996 | Erickson et al. |
| 5,571,190 A | | 11/1996 | Ulrich |
| 5,571,192 A | | 11/1996 | Schonhoffer |
| 5,573,529 A | | 11/1996 | Haak et al. |
| 5,593,409 A | | 1/1997 | Michelson |
| 5,601,556 A | | 2/1997 | Pisharodi |
| 5,609,636 A | | 3/1997 | Kohrs |
| 5,611,800 A | | 3/1997 | Davis et al. |
| 5,611,810 A | | 3/1997 | Arnold et al. |
| 5,632,747 A | | 5/1997 | Scarborough et al. |
| 5,645,598 A | | 7/1997 | Brosnahan et al. |
| 5,653,761 A | | 8/1997 | Pisharodi |
| 5,653,762 A | | 8/1997 | Pisharodi |
| 5,653,763 A | | 8/1997 | Errico et al. |
| 5,658,336 A | | 8/1997 | Pisharodi |
| 5,658,337 A | | 8/1997 | Kohrs et al. |
| 5,662,710 A | | 9/1997 | Bonutti |
| 5,665,122 A | | 9/1997 | Kambin |
| 5,669,909 A | | 9/1997 | Zdeblick et al. |
| 5,676,703 A | | 10/1997 | Gelbard |
| 5,683,394 A | | 11/1997 | Rinner |
| 5,683,400 A | | 11/1997 | McGuire |
| 5,683,464 A | | 11/1997 | Wagner et al. |
| 5,690,629 A | | 11/1997 | Asher et al. |
| 5,700,264 A | | 12/1997 | Zucherman et al. |
| 5,700,291 A | | 12/1997 | Kuslich et al. |
| 5,700,292 A | | 12/1997 | Marguilies |
| 5,702,449 A | | 12/1997 | McKay |
| 5,702,451 A | | 12/1997 | Biedermann et al. |
| 5,702,453 A | | 12/1997 | Rabbe et al. |
| 5,702,454 A | | 12/1997 | Baumgartner |
| 5,702,455 A | | 12/1997 | Saggar |
| 5,703,451 A | | 12/1997 | Yamamichi et al. |
| 5,707,373 A | | 1/1998 | Sevrain et al. |
| 5,711,957 A | | 1/1998 | Patat et al. |
| 5,716,415 A | | 2/1998 | Steffee |
| 5,720,748 A | | 2/1998 | Kuslich et al. |
| 5,720,751 A | | 2/1998 | Jackson |
| 5,723,013 A | | 3/1998 | Jeanson et al. |
| 5,728,159 A | * | 3/1998 | Stroever et al. ............... 623/23.5 |
| 5,741,261 A | | 4/1998 | Moscovitz et al. |
| 5,755,797 A | | 5/1998 | Baumgartner |
| 5,766,252 A | | 6/1998 | Henry et al. |
| 5,772,661 A | | 6/1998 | Michelson |
| 5,775,331 A | | 7/1998 | Raymond et al. |
| 5,776,199 A | | 7/1998 | Michelson |
| 5,779,642 A | | 7/1998 | Nightengale |
| 5,782,830 A | | 7/1998 | Farris |
| 5,782,919 A | | 7/1998 | Zdeblick et al. |
| 5,785,710 A | | 7/1998 | Michelson |
| 5,797,909 A | | 8/1998 | Michelson |
| 5,800,549 A | | 9/1998 | Bao et al. |
| 5,800,550 A | | 9/1998 | Sertich |
| 5,814,084 A | | 9/1998 | Grivas et al. |
| 5,851,208 A | | 12/1998 | Trott |
| 5,857,995 A | | 1/1999 | Thomas et al. |
| 5,860,973 A | | 1/1999 | Michelson |
| 5,861,041 A | | 1/1999 | Tienboon |
| 5,865,845 A | | 2/1999 | Thalgott |
| 5,865,847 A | | 2/1999 | Kohrs et al. |
| 5,865,848 A | | 2/1999 | Baker |
| 5,885,299 A | | 3/1999 | Winslow et al. |
| 5,888,219 A | | 3/1999 | Bonutti |
| 5,888,224 A | | 3/1999 | Beckers et al. |
| 5,888,227 A | | 3/1999 | Cottle |
| 5,893,890 A | | 4/1999 | Pisharodi |
| 5,904,719 A | | 5/1999 | Errico et al. |
| 5,910,315 A | | 6/1999 | Stevenson et al. |
| 5,954,769 A | | 9/1999 | Rosenlicht |
| 5,961,554 A | | 10/1999 | Janson et al. |
| 5,968,098 A | | 10/1999 | Winslow |
| 5,993,474 A | | 11/1999 | Ouchi |
| 6,004,326 A | | 12/1999 | Castro et al. |
| 6,015,436 A | | 1/2000 | Schunhuffer |
| 6,033,405 A | | 3/2000 | Winslow et al. |
| 6,033,438 A | | 3/2000 | Bianchi et al. |
| 6,039,761 A | | 3/2000 | Li et al. |
| 6,042,582 A | | 3/2000 | Ray |
| 6,045,580 A | | 4/2000 | Scarborough et al. |
| 6,048,342 A | | 4/2000 | Zucherman et al. |
| 6,059,790 A | | 5/2000 | Sand et al. |
| 6,063,088 A | | 5/2000 | Winslow |
| 6,083,225 A | | 7/2000 | Winslow et al. |
| 6,096,080 A | | 8/2000 | Nichols et al. |
| 6,102,948 A | | 8/2000 | Brosnahan, III |
| 6,102,950 A | | 8/2000 | Vaccaro |
| 6,117,174 A | | 9/2000 | Nolan |
| 6,120,506 A | | 9/2000 | Kohrs et al. |
| 6,126,689 A | | 10/2000 | Brett |
| 6,129,763 A | | 10/2000 | Chauvin et al. |
| 6,132,465 A | * | 10/2000 | Ray et al. ............... 623/17.16 |
| 6,132,472 A | | 10/2000 | Bonutti |
| 6,136,031 A | | 10/2000 | Middleton |
| 6,143,033 A | | 11/2000 | Paul et al. |
| 6,159,211 A | | 12/2000 | Boriani et al. |
| 6,159,215 A | | 12/2000 | Urbahns et al. |
| 6,165,219 A | | 12/2000 | Kohrs et al. |
| 6,171,339 B1 | | 1/2001 | Houfburg et al. |

(56) References Cited

U.S. PATENT DOCUMENTS

| | | |
|---|---|---|
| 6,174,311 B1 | 1/2001 | Branch et al. |
| 6,193,756 B1 | 2/2001 | Studer et al. |
| 6,200,322 B1 | 3/2001 | Branch et al. |
| 6,200,347 B1 | 3/2001 | Anderson |
| 6,210,412 B1 | 4/2001 | Michelson |
| 6,224,607 B1 | 5/2001 | Michelson |
| 6,224,631 B1 | 5/2001 | Kohrs |
| 6,238,397 B1 | 5/2001 | Zucherman et al. |
| 6,241,769 B1 | 6/2001 | Nicholson et al. |
| 6,241,770 B1 | 6/2001 | Michelson |
| 6,241,771 B1 | 6/2001 | Gresser et al. |
| 6,251,140 B1 | 6/2001 | Marino et al. |
| 6,258,125 B1 * | 7/2001 | Paul et al. .................. 623/17.11 |
| 6,261,296 B1 | 7/2001 | Aebi et al. |
| 6,264,656 B1 | 7/2001 | Michelson |
| 6,277,149 B1 | 8/2001 | Boyle et al. |
| 6,309,421 B1 | 10/2001 | Pisharodi |
| 6,319,257 B1 | 11/2001 | Carignan et al. |
| 6,364,880 B1 | 4/2002 | Michelson |
| 6,368,325 B1 | 4/2002 | McKinley et al. |
| 6,368,351 B1 | 4/2002 | Glenn et al. |
| 6,371,989 B1 | 4/2002 | Chauvin et al. |
| 6,402,785 B1 | 6/2002 | Zdeblick et al. |
| 6,436,140 B1 | 8/2002 | Liu et al. |
| 6,436,142 B1 | 8/2002 | Paes et al. |
| 6,440,142 B1 | 8/2002 | Ralph et al. |
| 6,440,170 B1 | 8/2002 | Jackson |
| 6,442,814 B1 | 9/2002 | Landry et al. |
| 6,443,987 B1 | 9/2002 | Bryan |
| 6,443,989 B1 | 9/2002 | Jackson |
| 6,454,806 B1 | 9/2002 | Cohen et al. |
| 6,454,807 B1 | 9/2002 | Jackson |
| 6,485,517 B1 | 11/2002 | Michelson |
| 6,491,724 B1 | 12/2002 | Ferree |
| 6,500,205 B1 | 12/2002 | Michelson |
| 6,524,318 B1 | 2/2003 | Longhini et al. |
| 6,527,773 B1 | 3/2003 | Lin et al. |
| 6,530,955 B2 | 3/2003 | Boyle et al. |
| 6,537,320 B1 | 3/2003 | Michelson |
| 6,558,423 B1 | 5/2003 | Michelson |
| 6,562,074 B2 | 5/2003 | Gerbec et al. |
| 6,589,247 B2 | 7/2003 | McGahan et al. |
| 6,595,998 B2 | 7/2003 | Johnson et al. |
| 6,599,292 B1 | 7/2003 | Ray |
| 6,610,065 B1 | 8/2003 | Branch et al. |
| 6,613,091 B1 | 9/2003 | Zdeblick et al. |
| 6,635,062 B2 | 10/2003 | Ray, III et al. |
| 6,635,086 B2 | 10/2003 | Lin |
| 6,648,895 B2 | 11/2003 | Burkus et al. |
| 6,652,584 B2 | 11/2003 | Michelson |
| 6,663,562 B2 | 12/2003 | Chang |
| 6,666,888 B1 | 12/2003 | Jackson |
| 6,666,889 B1 * | 12/2003 | Commarmond ............ 623/17.11 |
| 6,666,890 B2 | 12/2003 | Michelson |
| 6,685,742 B1 | 2/2004 | Jackson |
| 6,695,882 B2 | 2/2004 | Bianchi et al. |
| 6,699,288 B2 * | 3/2004 | Moret ......................... 623/17.16 |
| 6,706,070 B1 | 3/2004 | Wagner et al. |
| 6,709,458 B2 | 3/2004 | Michelson |
| 6,712,819 B2 | 3/2004 | Zucherman et al. |
| 6,716,245 B2 | 4/2004 | Pasquet et al. |
| 6,716,247 B2 | 4/2004 | Michelson |
| 6,719,794 B2 | 4/2004 | Gerber et al. |
| 6,723,128 B2 | 4/2004 | Uk |
| 6,730,126 B2 | 5/2004 | Boehm, Jr. et al. |
| 6,730,127 B2 | 5/2004 | Michelson |
| 6,740,091 B2 | 5/2004 | Kohrs et al. |
| 6,758,849 B1 | 7/2004 | Michelson |
| 6,773,460 B2 | 8/2004 | Jackson |
| 6,793,679 B2 | 9/2004 | Michelson |
| 6,808,537 B2 | 10/2004 | Michelson |
| 6,814,756 B1 | 11/2004 | Michelson |
| 6,821,298 B1 | 11/2004 | Jackson |
| 6,824,564 B2 | 11/2004 | Crozet |
| 6,830,570 B1 | 12/2004 | Frey et al. |
| 6,830,589 B2 | 12/2004 | Erickson |
| 6,833,006 B2 | 12/2004 | Foley et al. |
| 6,835,206 B2 | 12/2004 | Jackson |
| 6,852,126 B2 | 2/2005 | Ahlgren |
| 6,852,129 B2 | 2/2005 | Gerbec et al. |
| 6,863,673 B2 | 3/2005 | Gerbec et al. |
| 6,887,248 B2 | 5/2005 | McKinley et al. |
| 6,893,464 B2 | 5/2005 | Kiester |
| 6,902,566 B2 | 6/2005 | Zucherman et al. |
| 6,905,512 B2 | 6/2005 | Paes et al. |
| 6,921,403 B2 | 7/2005 | Cragg et al. |
| 6,923,814 B1 | 8/2005 | Hildebrand et al. |
| 6,923,830 B2 | 8/2005 | Michelson |
| 6,942,697 B2 * | 9/2005 | Lange et al. ............... 623/17.11 |
| 6,955,691 B2 | 10/2005 | Chae et al. |
| 6,962,606 B2 | 11/2005 | Michelson |
| 6,964,687 B1 | 11/2005 | Bernard |
| 6,972,035 B2 | 12/2005 | Michelson |
| 6,974,480 B2 | 12/2005 | Messerli et al. |
| 6,979,353 B2 | 12/2005 | Bresina |
| 7,004,945 B2 | 2/2006 | Boyd et al. |
| 7,022,137 B2 | 4/2006 | Michelson |
| 7,056,342 B2 | 6/2006 | Michelson |
| 7,112,206 B2 | 9/2006 | Michelson |
| 7,125,425 B2 | 10/2006 | Foley et al. |
| 7,137,997 B2 | 11/2006 | Paul |
| 7,156,875 B2 | 1/2007 | Michelson |
| 7,169,183 B2 * | 1/2007 | Liu et al. .................... 623/17.16 |
| 7,189,242 B2 | 3/2007 | Boyd et al. |
| 7,192,446 B2 | 3/2007 | Shapiro et al. |
| 7,223,292 B2 | 5/2007 | Messerli et al. |
| 7,225,698 B2 | 6/2007 | Bouche |
| 7,235,105 B2 | 6/2007 | Jackson |
| 7,238,203 B2 | 7/2007 | Bagga et al. |
| 7,267,689 B2 | 9/2007 | Kohrs |
| 7,288,093 B2 | 10/2007 | Michelson |
| 7,288,114 B2 * | 10/2007 | Lange ........................ 623/17.11 |
| 7,291,170 B2 | 11/2007 | Huppert |
| 7,316,686 B2 | 1/2008 | Dorchak et al. |
| 7,326,251 B2 | 2/2008 | McCombe et al. |
| 7,331,996 B2 | 2/2008 | Sato |
| 7,354,452 B2 | 4/2008 | Foley |
| 7,455,692 B2 | 11/2008 | Michelson |
| 7,470,273 B2 | 12/2008 | Dougherty-Shah |
| 7,479,160 B2 | 1/2009 | Branch et al. |
| 7,591,852 B2 | 9/2009 | Prosser |
| 7,608,080 B2 | 10/2009 | Shipp et al. |
| 7,621,958 B2 | 11/2009 | Zdeblick et al. |
| 7,637,953 B2 | 12/2009 | Branch et al. |
| 7,749,269 B2 | 7/2010 | Peterman et al. |
| 7,763,078 B2 | 7/2010 | Peterman et al. |
| 7,776,095 B2 | 8/2010 | Peterman et al. |
| 7,824,427 B2 | 11/2010 | Perez-Cruet et al. |
| 7,846,210 B2 | 12/2010 | Perez-Cruet et al. |
| 7,938,857 B2 | 5/2011 | Garcia-Bengochea et al. |
| 7,967,863 B2 * | 6/2011 | Frey et al. .................. 623/17.11 |
| 7,988,734 B2 | 8/2011 | Peterman et al. |
| 7,998,209 B2 | 8/2011 | Branch et al. |
| 8,012,208 B2 * | 9/2011 | Lechmann et al. ........ 623/17.11 |
| 8,025,684 B2 | 9/2011 | Garcia-Bengochea |
| 8,029,512 B2 | 10/2011 | Paltzer |
| 8,075,622 B2 | 12/2011 | Van Hoeck et al. |
| 8,092,537 B2 | 1/2012 | McGahan et al. |
| 8,287,597 B1 * | 10/2012 | Pimenta et al. ............ 623/17.16 |
| 2001/0010833 A1 | 8/2001 | Ray et al. |
| 2001/0020186 A1 | 9/2001 | Boyce et al. |
| 2002/0019637 A1 | 2/2002 | Frey et al. |
| 2002/0055781 A1 | 5/2002 | Sazy |
| 2002/0055782 A1 | 5/2002 | Bagby |
| 2002/0058950 A1 | 5/2002 | Winterbottom et al. |
| 2002/0065560 A1 | 5/2002 | Varga et al. |
| 2002/0082683 A1 | 6/2002 | Stinson et al. |
| 2002/0091447 A1 | 7/2002 | Shimp et al. |
| 2002/0099378 A1 | 7/2002 | Michelson |
| 2002/0111680 A1 | 8/2002 | Michelson |
| 2002/0143400 A1 | 10/2002 | Biscup |
| 2003/0040798 A1 | 2/2003 | Michelson |
| 2003/0100950 A1 * | 5/2003 | Moret ........................ 623/17.16 |
| 2003/0105528 A1 | 6/2003 | Shimp et al. |

(56) References Cited

U.S. PATENT DOCUMENTS

| | | |
|---|---|---|
| 2003/0125739 A1 | 7/2003 | Bagga et al. |
| 2003/0135275 A1 | 7/2003 | Garcia et al. |
| 2003/0139813 A1 | 7/2003 | Messerli et al. |
| 2003/0149438 A1 | 8/2003 | Nichols et al. |
| 2003/0176924 A1 | 9/2003 | Burdett |
| 2003/0195632 A1 | 10/2003 | Foley et al. |
| 2003/0233147 A1 | 12/2003 | Nicholson et al. |
| 2004/0143332 A1 | 7/2004 | Krueger et al. |
| 2004/0158327 A1 | 8/2004 | Bagby |
| 2005/0038512 A1 | 2/2005 | Michelson |
| 2005/0049706 A1 | 3/2005 | Brodke et al. |
| 2005/0096745 A1 | 5/2005 | Andre et al. |
| 2005/0143822 A1* | 6/2005 | Paul ............... 623/17.16 |
| 2005/0149194 A1 | 7/2005 | Ahlgren |
| 2005/0216082 A1 | 9/2005 | Wilson et al. |
| 2005/0245937 A1 | 11/2005 | Winslow |
| 2005/0273172 A1 | 12/2005 | Patil et al. |
| 2006/0009845 A1 | 1/2006 | Chin |
| 2006/0085072 A1 | 4/2006 | Funk et al. |
| 2006/0106460 A1 | 5/2006 | Messerli et al. |
| 2006/0212120 A1 | 9/2006 | McGahan et al. |
| 2006/0241760 A1 | 10/2006 | Randall et al. |
| 2006/0247638 A1 | 11/2006 | Trieu et al. |
| 2006/0247775 A1 | 11/2006 | Thramann et al. |
| 2007/0016303 A1 | 1/2007 | Jackson |
| 2007/0093897 A1 | 4/2007 | Gerbec et al. |
| 2007/0173821 A1 | 7/2007 | Trieu |
| 2007/0191946 A1 | 8/2007 | Heinz et al. |
| 2007/0233247 A1 | 10/2007 | Schwab |
| 2007/0255416 A1 | 11/2007 | Melkent et al. |
| 2007/0270950 A1 | 11/2007 | Trieu |
| 2007/0270963 A1 | 11/2007 | Melkent et al. |
| 2007/0293949 A1 | 12/2007 | Salerni et al. |
| 2008/0015701 A1 | 1/2008 | Garcia et al. |
| 2008/0058808 A1 | 3/2008 | Klyee et al. |
| 2008/0058933 A1 | 3/2008 | Garner et al. |
| 2008/0065219 A1* | 3/2008 | Dye ............... 623/17.16 |
| 2008/0065291 A1 | 3/2008 | Breed |
| 2008/0077247 A1* | 3/2008 | Murillo et al. ............ 623/17.16 |
| 2008/0097610 A1 | 4/2008 | Guyer et al. |
| 2008/0114467 A1 | 5/2008 | Capote et al. |
| 2008/0154375 A1* | 6/2008 | Serhan et al. ............ 623/17.16 |
| 2008/0161927 A1 | 7/2008 | Savage et al. |
| 2008/0183292 A1 | 7/2008 | Trieu |
| 2008/0249622 A1* | 10/2008 | Gray ............... 623/17.11 |
| 2008/0275506 A1 | 11/2008 | Baynham et al. |
| 2009/0105821 A1 | 4/2009 | Michelson |
| 2010/0152853 A1* | 6/2010 | Kirschman ............ 623/17.11 |

FOREIGN PATENT DOCUMENTS

| | | |
|---|---|---|
| EP | 517030 | 5/1992 |
| EP | 667127 | 8/1995 |
| EP | 706876 | 4/1996 |
| EP | 716840 | 6/1996 |
| EP | 737448 | 10/1996 |
| EP | 796593 | 9/1997 |
| EP | 880938 | 2/1998 |
| EP | 809974 | 4/1998 |
| EP | 809975 | 4/1998 |
| EP | 811356 | 4/1998 |
| EP | 732093 | 11/2004 |
| EP | 1504732 | 5/2007 |
| EP | 1400221 | 9/2011 |
| FR | 2813519 | 3/2002 |
| WF | 91/06261 | 5/1991 |
| WO | 94/04100 | 3/1994 |
| WO | 94/10928 | 5/1994 |
| WO | 95/01810 | 1/1995 |
| WO | 96/08205 | 3/1996 |
| WO | 96/17564 | 3/1996 |
| WO | 96/41582 | 12/1996 |
| WO | 97/20513 | 6/1997 |
| WO | 97/33525 | 9/1997 |
| WO | 97/37620 | 10/1997 |
| WO | 98/09586 | 3/1998 |
| WO | 98/14142 | 4/1998 |
| WO | 98/17208 | 4/1998 |
| WO | 98/25539 | 6/1998 |
| WO | 99/08627 | 2/1999 |
| WO | 99/38461 | 8/1999 |
| WO | 00/45712 | 8/2000 |
| WO | 00/45713 | 8/2000 |
| WO | 00/66045 | 11/2000 |
| WO | 01/41681 | 6/2001 |
| WO | 01/49333 | 7/2001 |
| WO | 02/17823 | 3/2002 |
| WO | 02/058593 | 8/2002 |
| WO | 02/076335 | 10/2002 |

OTHER PUBLICATIONS

Benini et al., "Undercutting decompression and posterior fusion with translaminar facet screw fixation in degenerative lumbar spinal stenosis: Technique and results," *Neuro-Orthopedics*, 1995, 159-172.

Kambin et al., "History and current status of percutaneous arthroscopic disc surgery," 1996, *Spine 21*, 57S-61S.

Stein et al., Percutaneous facet joint fusion: Preliminary experience, *Journal of Vascular and Interventional Radiology*, 4, 1993, 69-74.

Vamvanij et al., "Surgical treatment of internal disc disruption: An outcome study of four fusion techniques," *Journal of Spinal Disorders*, 4, 1998, 375-382.

* cited by examiner

SPINAL FUSION IMPLANT AND RELATED METHODS

CROSS REFERENCES TO RELATED APPLICATIONS

The present application is a continuation-in-part of application Ser. No. 11/488,744, filed on Jul. 17, 2006 now U.S. Pat. No. 7,867,277, which claims the benefit of priority from U.S. Provisional Application Ser. No. 60/699,597, filed on Jul. 15, 2005, the entire contents of each are hereby expressly incorporated by reference into this disclosure as if set forth fully herein.

BACKGROUND OF THE INVENTION

I. Field of the Invention

The present invention relates generally to spinal surgery and, more particularly, to a device for spinal fusion comprising a spinal fusion implant of non-bone construction to be introduced into any variety of spinal target sites.

II. Discussion of the Prior Art

Currently there are somewhere between 500,000 and 750,000 lumbar and cervical spinal fusion procedures performed each year in the United States. One of the causes of back pain and disability derives from the rupture or degeneration of one or more intervertebral discs in the spine. Surgical procedures are commonly performed to correct problems with displaced, damaged, or degenerated intervertebral discs due to trauma, disease, or aging. Generally, spinal fusion procedures involve removing some or the all of the diseased or damaged disc, and inserting one or more intervertebral implants into the resulting disc space.

Minimally invasive methods of performing spinal fusion have gained popularity in recent years due to the many benefits of the procedure which include diminished dissection of body tissue and lower blood loss during surgery resulting in reduced surgery time, lower post-operative pain and a quicker recovery for patients. Transforaminal lumbar interbody fusion (TLIF) procedures provide unilateral access to a desired target site. The TLIF technique involves approaching the spine in a similar manner as a posterior approach but more from the left or right of the spine through a midline incision in a patient's back. This procedure requires only one incision in the back of a patient and involves placing a fusion device into the intervertebral disc space. Introducing the intervertebral implant serves to restore the height between adjacent vertebrae ("disc height"), which reduces if not eliminates neural impingement commonly associated with a damaged or diseased disc. Distraction of the disc space with subsequent decompression of nerve roots can be accomplished by rotating a device between the adjacent vertebrae.

Current spinal fusion implants utilize either bone grafts or artificial implants to fill the intervertebral disc space. Artificial implants may be made of metal, plastic composites, ceramics, bone, or any combination thereof. Natural bone grafts have also been developed including autologous and allograft bone. Other bone grafts may include certain man-made substances including binder joining bone chips and composite bone structures.

While generally effective, the use of bone grafts presents several disadvantages. Autologous bone grafts are obtained from bone material surgically removed from the iliac crest of a patient. This method can be detrimental because it may not yield a sufficient quantity of graft material, requires additional surgery, and increases the risk of infection and blood loss. Moreover, the structural integrity at the donor site can be reduced and significant morbidity associated with harvesting the autologous bone graft may occur.

Allograft bone is obtained from cadaveric specimens, machined, and sterilized for implantation. Production of allograft bone implants may be difficult because of the inherent challenges in forecasting the receipt of cadavers. Furthermore, allograft may only provide temporary support as it is difficult to manufacture the allograft with consistent shape and strength given the differing characteristics of cadavers. Graft material usually has a smooth surface which does not provide good friction between the adjacent vertebrae and slippage of the graft may occur which can cause neural and vascular injury as well as collapse of the disc space.

A need remains for fusion implants that preserve the intradiscal space and support the vertebral column until the adjacent vertebrae are fused and still encourage bone ingrowth to achieve a solid fusion. A need also remains for implants which maximize cortical ring contact (both anteriorly and posteriorly), better facilitate self distraction of the vertebrae during insertion, avoid dural impingement and provide a better fit between anterior edge portions of vertebral endplates.

The present invention is directed at overcoming, or at least minimizing, the disadvantages of the prior art.

SUMMARY OF THE INVENTION

The present invention overcomes the drawbacks of the prior art by providing a spinal fusion implant of non-bone construction. The non-bone construction of the spinal fusion implant provides an advantage in that it is not supply limited and does not require harvesting bone from the patient (as with allograft). The present invention better facilitates cortical ring contact and fit between anterior ring portions of vertebral endplates, provides-self distraction during insertion and rotation, and avoids dural impingement.

The spinal fusion implant of the present invention may be comprised of any suitable non-bone composition, including but not limited to polymer compositions (e.g. poly-ether-ether-ketone (PEEK) and/or poly-ether-ketone-ketone (PEKK)), ceramic, metal, or any combination of these materials. The spinal fusion implant of the present invention may be provided in any number of suitable shapes and sizes depending upon the particular surgical procedure or need. The spinal fusion implant may be dimensioned for use in any part of the spine (e.g. cervical, lumbar and/or thoracic) without departing from the scope of the present invention. The implant may be dimensioned, by way of example only, having a width ranging between 8 and 14 mm, a height ranging between 8 and 18 mm, and a length ranging between 25 and 45 mm.

According to one broad aspect of the present invention, the spinal fusion implant includes a top surface, a bottom surface, lateral sides, a proximal end, and a distal end. The spinal fusion implant of the present invention may be used to provide temporary or permanent fixation along an orthopedic target site. To do so, the spinal fusion implant may be introduced into a disc space while locked to a surgical insertion instrument and thereafter manipulated in the proper orientation and released. Once deposited in the disc space, the spinal fusion implant of the present invention effects fusion over time as the natural healing process integrates and binds the implant.

The spinal fusion implant of the present invention may be provided with any number of additional features for promoting fusion, such as one or more apertures extending between the top and bottom surfaces which allow a boney bridge to form through the spinal fusion implant. The spinal implant may also be preferably equipped with one or more lateral openings which facilitate visualization at the time of implantation and at subsequent clinical evaluations.

The spinal fusion implant may also be provided with any number of suitable anti-migration features to prevent the implant from migrating or moving from the disc space after implantation. Suitable anti-migration features may include, but are not necessarily limited to, angled teeth or ridges formed along the top and bottom surfaces of the implant and/or rod elements disposed within the distal and/or proximal ends.

According to a further aspect of the present invention, the spinal fusion implant may be provided with a variable height along at least a portion of the implant. In one embodiment, the variable height tapers in a direction oblique to both the length and width of the implant. The oblique taper imparts a greater height to the anterior aspect of the intervertebral disc space when the spinal fusion implant is positioned obliquely within the disc space. Imparting a greater height to the anterior aspect of the disc space restores the natural lordotic curvature of the lumbar (as well as cervical) spine.

According to a further aspect of the present invention, the spinal fusion implant may be provided with one or more radiographic markers at the proximal and/or distal ends. These markers allow for a more detailed visualization of the implant after insertion (through radiography) and allow for a more accurate and effective placement of the implant.

According to a still further aspect of the present invention, the proximal end of the spinal fusion implant has a surface that is tapered (angled) to avoid dural impingement after implantation. Additionally, the tapered nature of the proximal surface can aid in overall fit of the spinal fusion implant within the intervertebral disc space. Significantly, the tapered proximal surface on the proximal end enables the spinal fusion implant 10 to maximize contact with the posterior portion of the cortical ring of each adjacent vertebral body.

According to a still further aspect of the present invention, the distal end of the spinal fusion implant has a conical (bullet-shaped) shape including a pair of first tapered (angled) surfaces and a pair of second tapered (angled) surfaces. The first tapered surfaces extend between the lateral surfaces and the distal end of the implant, and function to distract the vertebrae adjacent to the target intervertebral space during insertion of the spinal fusion implant. The second tapered surfaces extend between the top and bottom surfaces and the distal end of the spinal fusion implant, and function to maximize contact with the anterior portion of the cortical ring of each adjacent vertebral body. Furthermore, the second tapered surfaces provide for a better fit with the contour of the vertebral body endplates, allowing for a more anterior positioning of the spinal fusion implant and thus advantageous utilization of the cortical rings of the vertebral bodies.

According to a still further aspect of the present invention, the spinal fusion implant may be introduced into a spinal target site through use of any of a variety of suitable surgical instruments having the capability to engage the implant. The spinal fusion implant is capable of being used in minimally invasive surgical procedures, needing only a relatively small operative corridor for insertion.

According to a still further aspect of the present invention, once the implant has been positioned in its desired location within the intervertebral space, the user will then rotate the implant 90° such that the top and bottom surfaces face in a caudad/cephalad direction and the anti-migration features engage the vertebral bodies. Significantly, the direction of rotation is critical to ensure proper placement of the implant such that the edges of the proximal surface rest on the cortical ring of the vertebral bodies and the proximal surface does not protrude into the spinal canal. For example, if the spinal fusion implant approaches a patient's spine posteriorly from the right with the (longer) first lateral side facing caudally, then implant must be rotated in a counter-clockwise direction to achieve proper positioning.

According to a still further aspect of the present invention, one or more of the spinal fusion implants of the present invention may be used in a variety of configurations in a fusion procedure, including but not limited to (and by way of example only) unilateral, paired unilateral and bilateral.

In a unilateral configuration, a single spinal fusion implant of the present invention is inserted into an intervertebral disc space and positioned obliquely across the disc space such that the proximal and distal ends are on opposite sides of the midline of the intervertebral space.

In a paired unilateral configuration, a first spinal fusion implant is inserted into the disc space and positioned obliquely within the intervertebral space, but not necessarily directly across the midline. A second spinal fusion implant is then inserted directly adjacent to the first implant such that the implants are in a side-by-side position.

In a bilateral configuration, a first spinal fusion implant is inserted into the disc space, positioned obliquely, and disposed entirely on one side of the midline of the intervertebral space. A second spinal fusion implant is the inserted into the disc space from the mirror-image postero-lateral approach such that the second spinal fusion implant occupies the portion of the intervertebral space on the opposite side of the midline from the first spinal fusion implant.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal fusion implant disclosed herein boasts a variety of inventive features and components that warrant patent protection, both individually and in combination.

Figure 1:
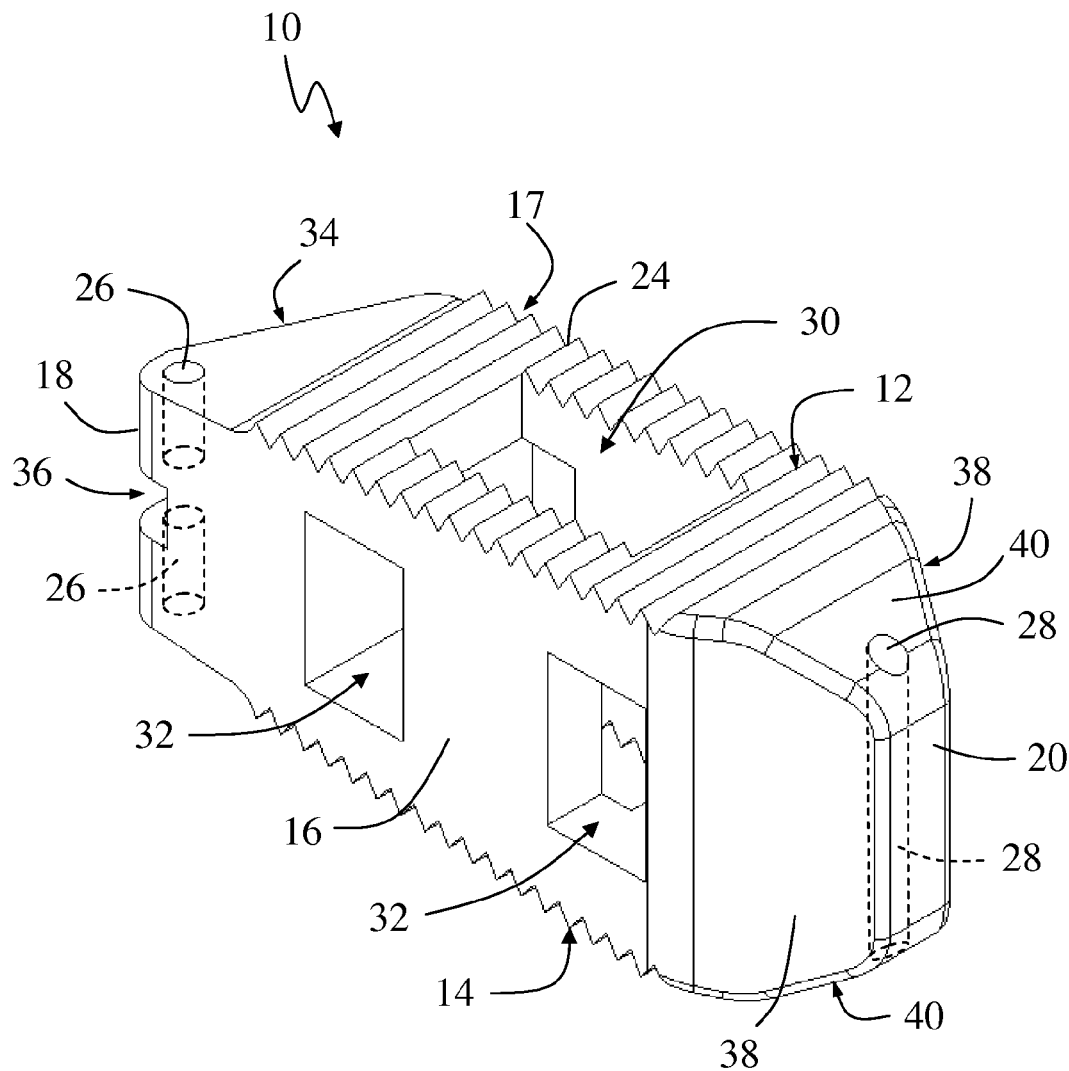
FIG. 1 is a perspective view of an example of a spinal fusion implant according to one embodiment of the present invention.

FIG. 1 illustrates a spinal fusion implant 10 according to a first broad aspect of the present invention. The spinal fusion implant 10 may be constructed of any suitable non-bone composition, including but not limited to polymer compositions (e.g. poly-ether-ether-ketone (PEEK) and/or poly-ether-ketone-ketone (PEKK)), ceramic, metal and/or any combination of polymer compositions, ceramic and metal. The spinal fusion implant 10 of the present invention may be provided in any number of shapes and sizes depending upon the particular surgical procedure or need. By way of example only, the spinal fusion implant 10 may have a width ranging between 8 and 14 mm, a height ranging between 8 and 18 mm, and a length ranging between 25 and 45 mm.

The spinal fusion implant 10 of the present invention includes a top surface 12, a bottom surface 14, first and second lateral sides 16, 17, a proximal (posterior) end 18 and a distal (anterior) end 20. The spinal fusion implant 10 of the present invention may be used to provide temporary or permanent fixation within an orthopedic target site. To do so, the spinal fusion implant 10 may be introduced into a disc space while locked to a surgical insertion instrument and thereafter employed in the proper orientation and released, as explained in further detail below. Once deposited in the disc space, the spinal fusion implant 10 of the present invention effects spinal fusion over time as the natural healing process integrates and binds the implant.

Figure 2:
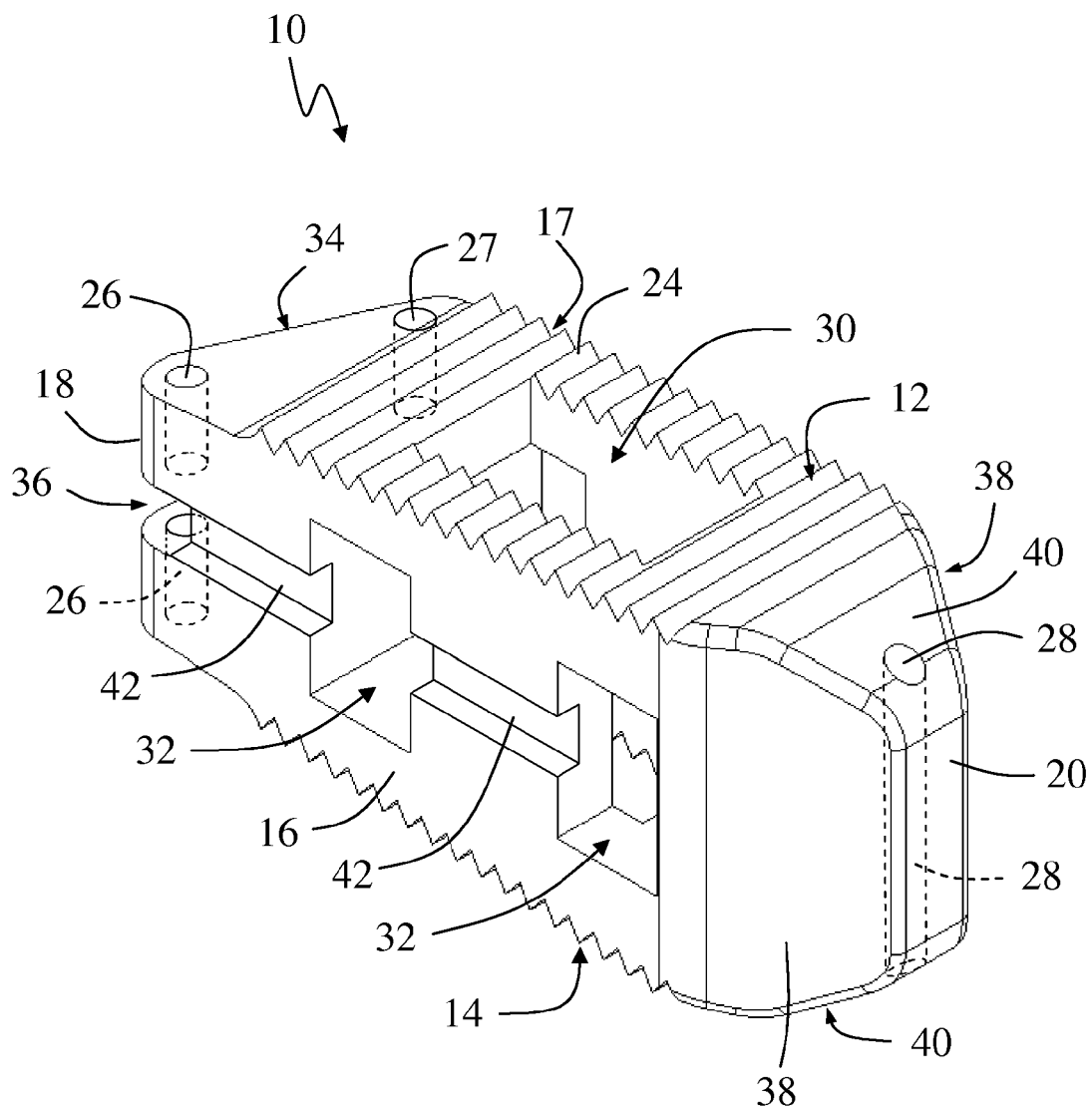
FIG. 2 is a perspective view of an example of a spinal fusion implant according to an alternative embodiment of the present invention.

FIG. 2 illustrates a spinal fusion implant 10 according to an alternative embodiment of the present invention, having slightly different (and optional) features than the spinal fusion implant of FIG. 1. Specifically, as will be discussed in greater detail below, the spinal fusion implant 10 of FIG. 2 is provided with an additional radiographic marker 27 at the proximal end and lateral recesses 42 for engagement with an insertion device.

Figure 3:
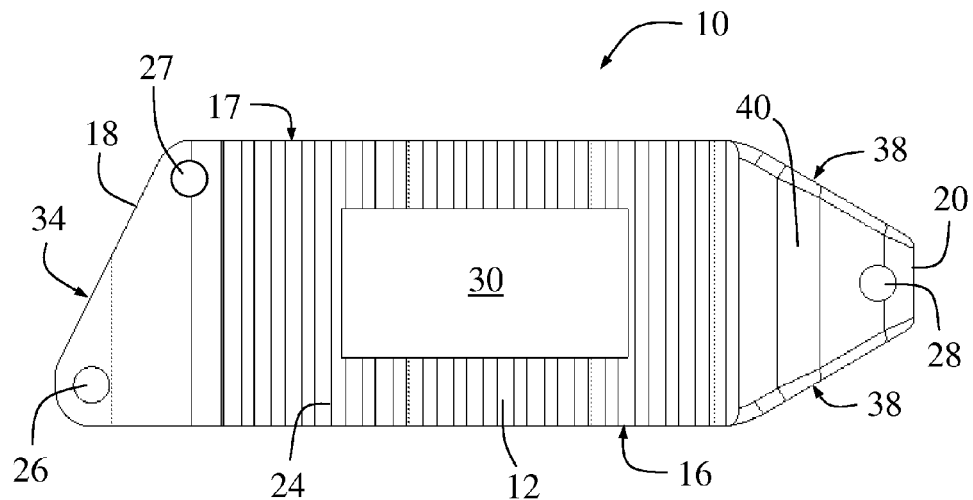
FIG. 3 is a top view of the spinal fusion implant of FIG. 2.
Figure 4:
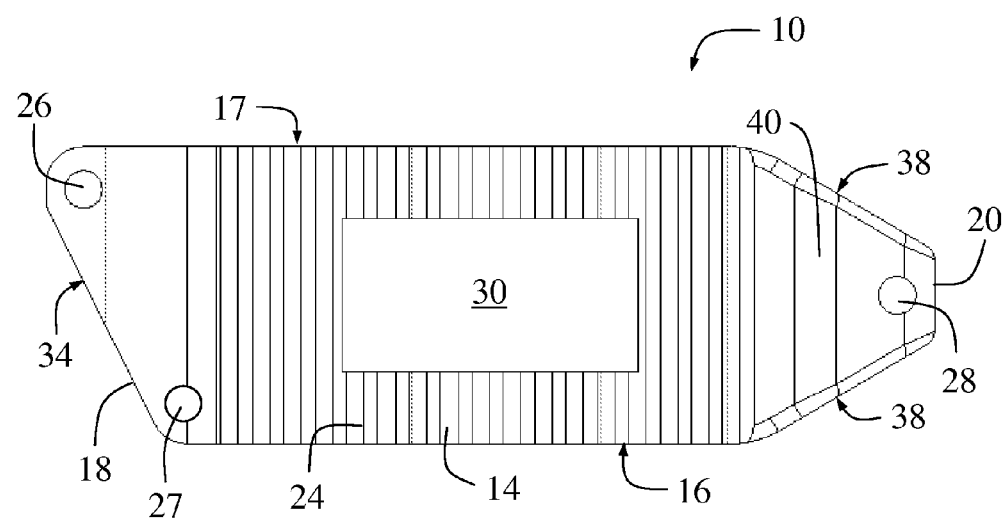
FIG. 4 is a bottom view of the spinal fusion implant of FIG. 2.
Figure 5:
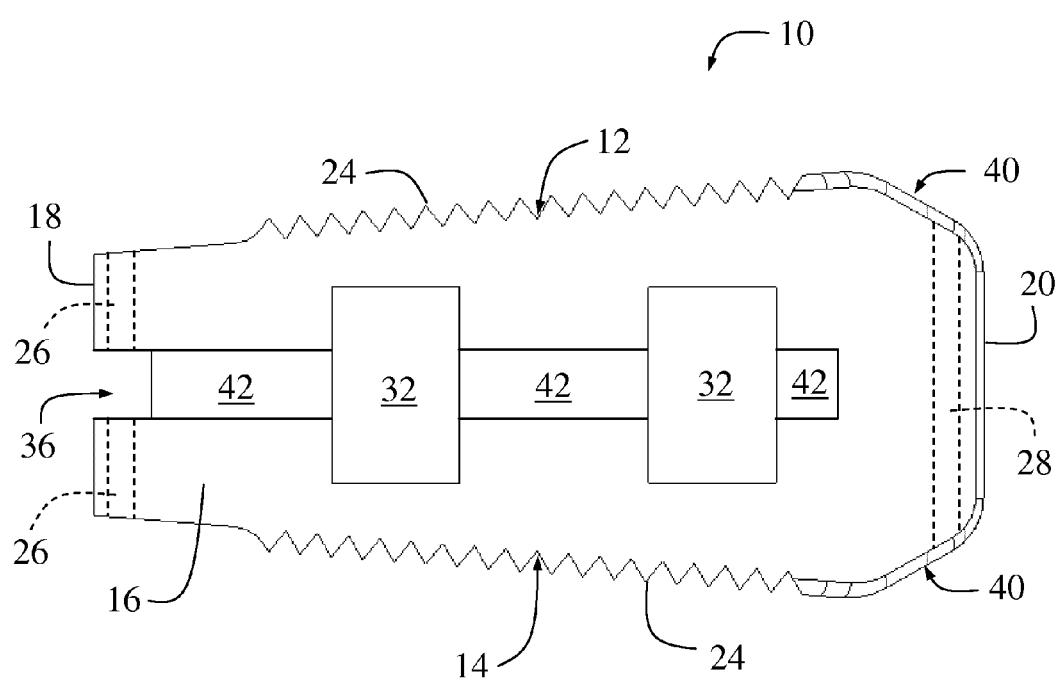
FIG. 5 is a side view of the spinal fusion implant of FIG. 2.
Figure 8:
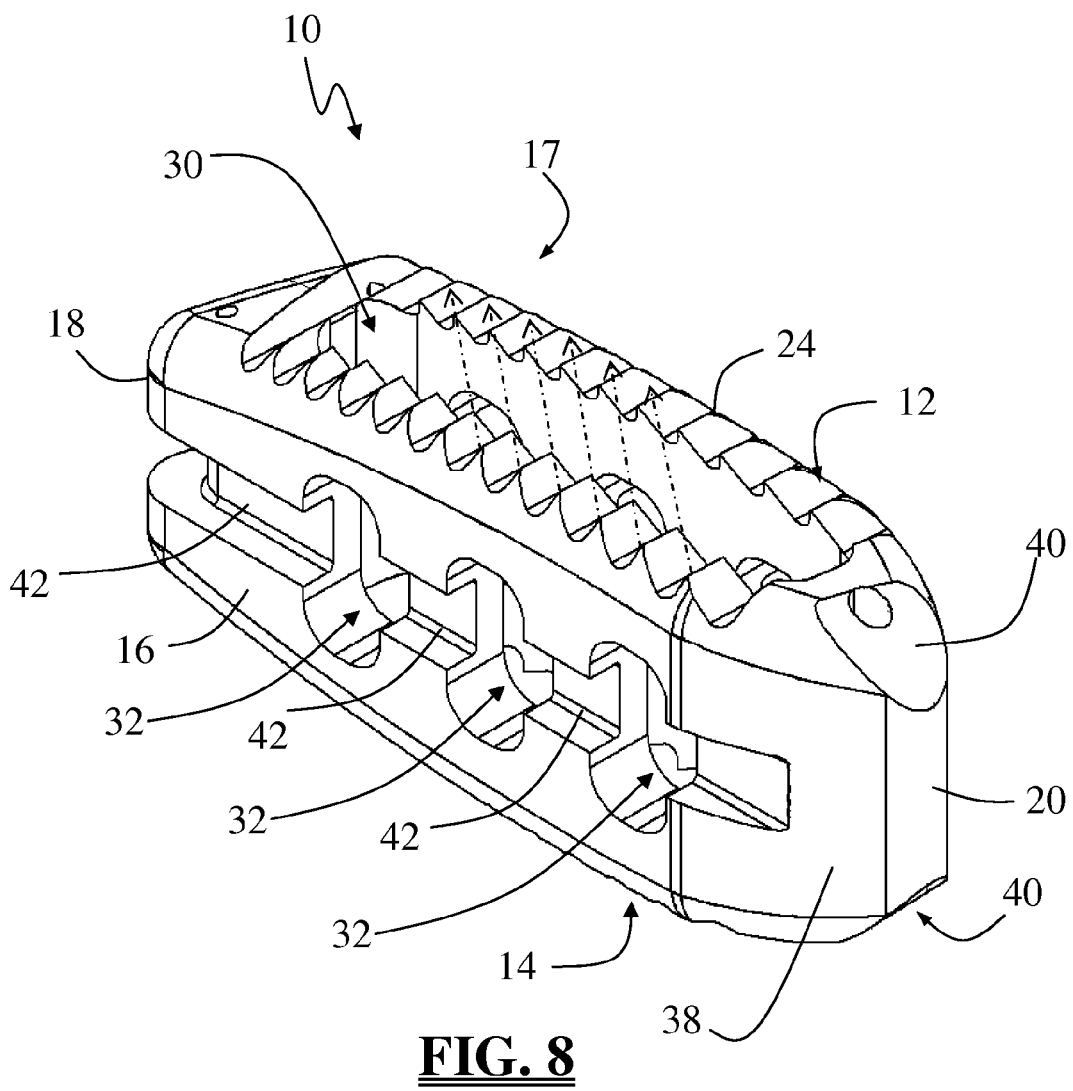
FIG. 8 is a perspective view of an example of a spinal fusion implant according to an alternative embodiment of the present invention.
Figure 9:
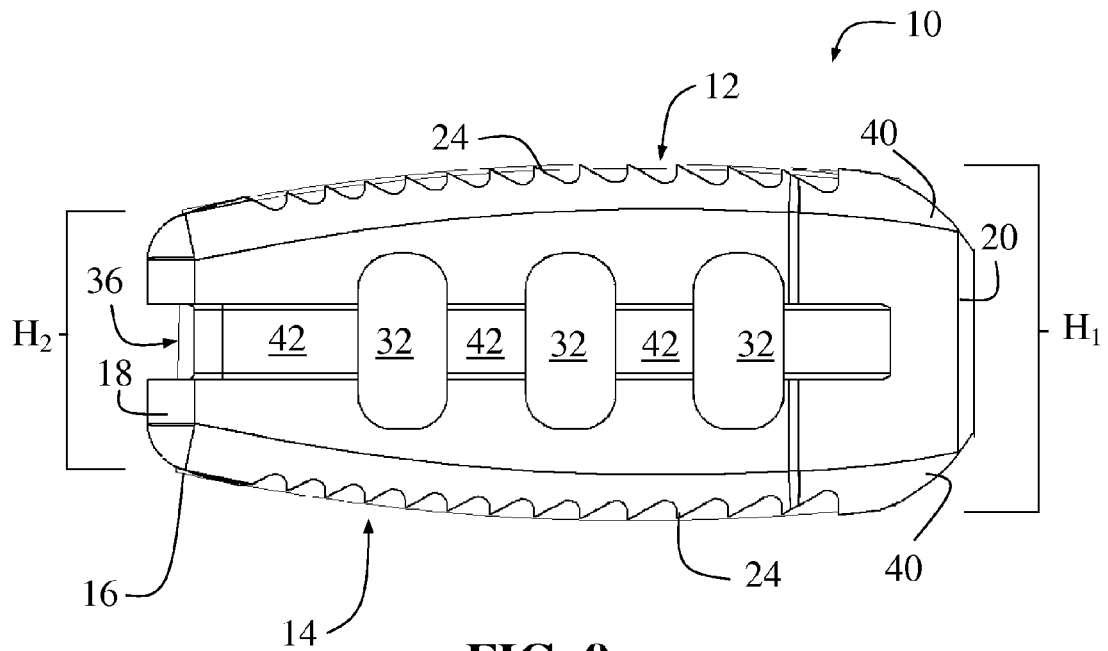
FIG. 9 is a side view of the spinal fusion implant of FIG. 8.
Figure 10:
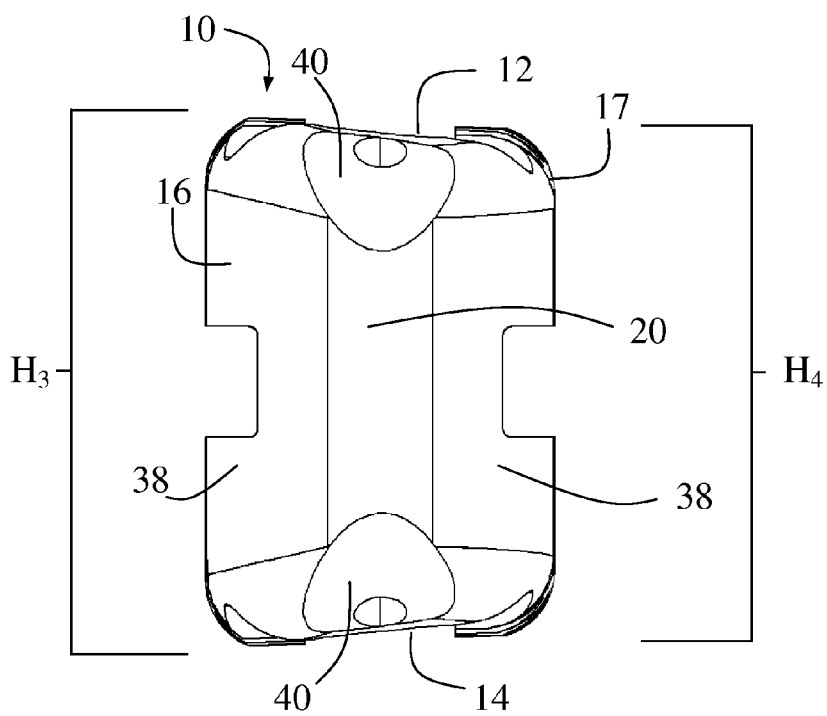
FIG. 10 is a plan view of a proximal end view of the spinal fusion implant of FIG. 9.

FIGS. 3-4 illustrate the top and bottom surfaces 12, 14, respectively, of the spinal fusion implant 10. As best depicted in FIG. 5, the top and bottom surfaces 12, 14 are not generally parallel to each other and may be angled or tapered from distal (anterior) end 20 to proximal (posterior) end 18. As such, the spinal fusion implant 10 of the present invention has a variable height along the length of the implant, as measured by the distance between the top and bottom surfaces 12, 14. By way of example only, this taper or incline may have a measured angle between 5 and 10 degrees. The practical result of this tapering is that the spinal fusion implant 10 has an anterior height that is greater than the posterior height to help restore the natural lordotic curvature of the lumbar spine. An alternative embodiment, discussed below, may have a variable height that tapers oblique to the length and width of the implant to restore more accurately the lordotic curvature when the implant is placed obliquely within the disc space. It can be appreciated by one skilled in the art that the top and bottom surfaces 12, 14 may be configured in any number of suitable shapes to better match the natural contours of the vertebral end plates. For example, although the top and bottom surfaces 12, 14 are shown in the FIGS. 1-7 as being generally planar, other configurations, such as for example generally concave and/or convex (as illustrated in the embodiment of FIGS. 8-10) are possible.

The top and bottom surfaces 12, 14 are configured to engage the vertebral bodies adjoining the target disc space. Accordingly, the top and bottom surfaces 12, 14 each preferably include a plurality of anti-migration features designed to increase the friction between the spinal fusion implant 10 and the adjacent contacting surfaces of the vertebral bodies. Such anti-migration features may include ridges (or teeth) 24 provided along the top surface 12 and/or bottom surface 14. The friction prohibits migration of the implant 10 after insertion into the intervertebral space and during the propagation of natural bony fusion. It should be appreciated by one skilled in the art that such ridges (or teeth) 24 can be oriented in a particular direction which will stabilize the implant in several degrees of rotation during placement.

The spinal fusion implant 10 of the present invention may also be provided with one or more radiographic markers to allow for visual determination of proper implant placement. As best appreciated in FIGS. 1, 2 and 5, the proximal end 18 of implant 10 may be provided with at least a pair of radiographic markers 26, each extending between one of the top and bottom surfaces 12, 14 and the proximal engagement recess 36. Preferably, radiographic markers 26 are positioned near the intersection of first lateral side 16 and proximal surface 34. Optionally, as shown in FIG. 2, the proximal implant 18 may be further provided with a pair of radiographic markers 27, each extending between one of the top and bottom surfaces 12, 14 and the proximal engagement recess 36. Preferably, radiographic markers 27 are positioned near the intersection of second lateral side 17 and proximal surface 34. The distal end 20 may be provided with radiographic marker 28 comprising a unitary element fully extending between the top and bottom surfaces 12, 14.

The radiographic markers 26, 27, 28 may be provided in any size or shape suitable to facilitate effective and accurate visualization of implant placement. For example, the spinal fusion implant 10 shown in FIGS. 1-7 include radiographic markers 26, 27, 28 in the form of elongated cylinders extending generally perpendicularly through the implant 10 between the top and bottom surfaces 12, 14. Alternatively, radiographic markers 26, 27, 28 may include a shorter element which extends only partially from either the top surface 12 or the bottom surface 14 (that is, does not extend through the entire height of the implant 10). As a further alternative, radiographic markers 26, 27, 28 may extend at least partially (but not fully) toward either or both of top and bottom surfaces 12, 14 (that is, radiographic markers 26, 28 may be disposed completely within the body of the implant 10).

The radiographic markers 26, 28 may be manufactured from any of a variety of suitable radiopaque materials, including but not limited to a metal, ceramic, and/or polymer material, preferably having radiopaque characteristics.

The spinal fusion implant 10 includes a large aperture 30 extending between top and bottom surfaces 12, 14. FIGS. 1-4 illustrate aperture 30 extending in a vertical fashion between the top and bottom surfaces 12, 14. The aperture 30 may be provided in any number of suitable shapes, including but not limited to generally circular, generally oblong, generally triangular and/or generally rectangular (as shown by example in FIGS. 3 and 4). This single aperture 30 is an additional feature for promoting fusion between the upper and lower vertebral bodies which allow a boney bridge to form through the spinal fusion implant 10.

According to another further aspect of the present invention, this fusion may be facilitated or augmented by including osteoinductive material(s) within the aperture 30 and/or adjacent to the spinal fusion implant 10. Such osteoinductive materials may be introduced before, during, or after insertion of the spinal fusion implant 10 of the present invention, and may include (but are not necessarily limited to) autologous bone harvested from the patient receiving the spinal fusion implant 10, bone allograft, bone xenograft, any number of non-bone implants (e.g. ceramic, metallic, polymer), bone morphogenic protein, and bio-resorbable compositions, including but not limited to any of a variety of poly (D, L-lactide-co-glycolide) based polymers, such as those disclosed in U.S. Pat. No. 6,013,853.

FIG. 5 depicts the spinal fusion implant 10 from a side view. First and second lateral sides 16, 17 are generally parallel to one another (shown best in FIGS. 3-4). Preferably, the first lateral side 16 has a greater length than the second lateral side 17. The effect of this disparity is to cause the proximal surface 34 to be angled or tapered from the first lateral surface 16 to the second lateral surface 17. This angular surface provides an advantage by allowing an oblique positioning of the spinal fusion implant 10 within the intervertebral space, without protruding into the spinal canal, as will be explained in greater detail below. The spinal fusion implant 10 may be further provided with one or more lateral apertures 32 extending generally perpendicularly therethrough from one lateral side 16 to the other. Lateral apertures 32 function to provide visualization at the time of implantation and at subsequent clinical evaluations. Lateral apertures 32 may be provided in any of a variety of suitable shapes, including but not limited to generally circular, generally oblong, generally triangular and/or generally rectangular (shown by example in FIG. 5), or any combination thereof. Although the spinal fusion implant 10 examples shown in FIGS. 1-2 each include a pair of lateral apertures 32, the spinal fusion implant 10 may include any number of lateral apertures 32 as desired.

More specifically, based on the generally radiolucent nature of the implant 10, the lateral apertures 32 provide the ability to visualize the interior of the implant 10 during X-ray and/or other suitable imaging techniques which are undertaken from the lateral (or "side") perspective of the implant 10. If fusion has taken place, the lateral apertures 32 will provide a method for the surgeon to make follow up assessments as to the degree of fusion without any visual interference from the spinal fusion implant 10. Further, the lateral apertures 32 will provide an avenue for cellular migration to the exterior of the spinal fusion implant 10. Thus the spinal fusion implant 10 will serve as additional scaffolding for bone fusion on the exterior of the spinal fusion implant 10.

Figure 6:
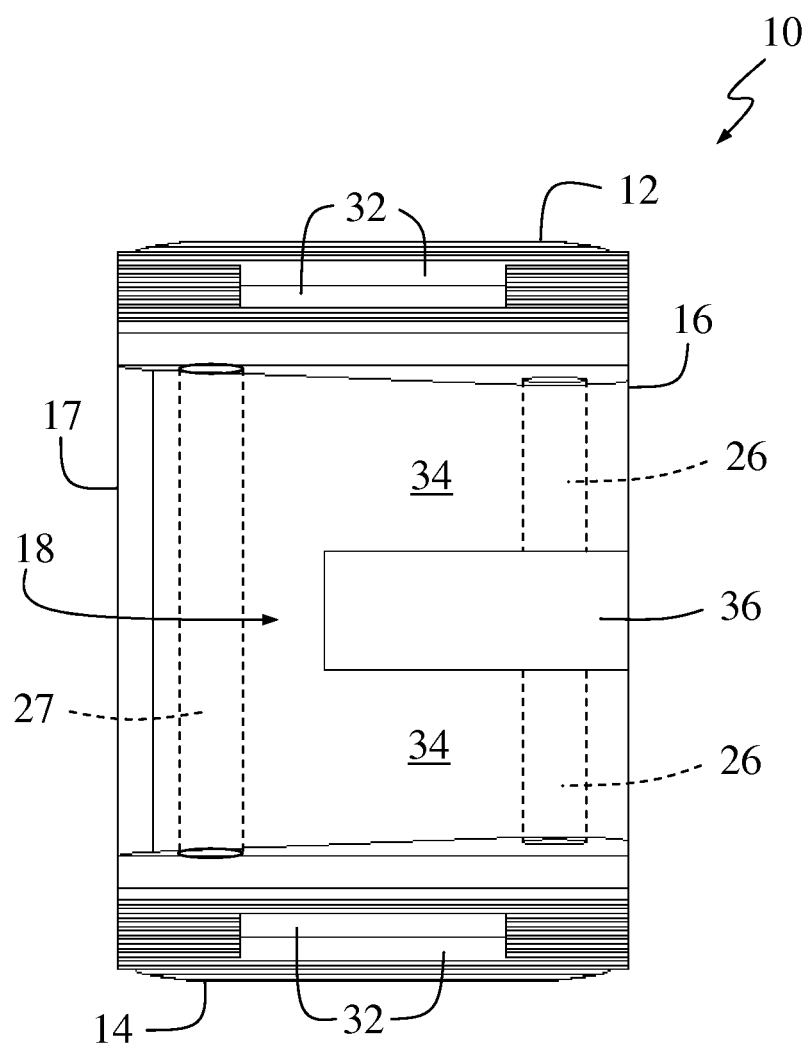
FIG. 6 is a plan view of a distal end of the spinal fusion implant of FIG. 2.

FIG. 6 illustrates the proximal end 18 of the spinal fusion implant 10 of the present invention. The proximal end 18 has a proximal surface 34 that is tapered (angled) to avoid dural impingement after insertion (as best illustrated in FIGS. 1-4). Additionally, the tapered nature of the proximal surface 34 can aid in overall fit of the spinal fusion implant 10 within the vertebral disc space. Significantly, the tapered proximal surface 34 on the proximal end 18 enables the spinal fusion implant 10 to maximize contact with the posterior portion of the cortical ring of each adjacent vertebral body. The proximal end 18 may include a proximal engagement recess 36 which extends inwardly in a generally perpendicular fashion relative to the proximal end 18. Although shown as having a generally rectangular cross-section, it will be appreciated that the proximal engagement recess 36 may be provided having any number of suitable shapes or cross-sections, including but not limited to circular or triangular. Furthermore, the proximal engagement recess 36 may extend fully or at least partially along the length of the proximal surface 34. Proximal engagement recess 36 is dimensioned to receive and engage with an insertion tool (not shown) for inserting the spinal fusion implant 10 into the intervertebral space.

Figure 7:
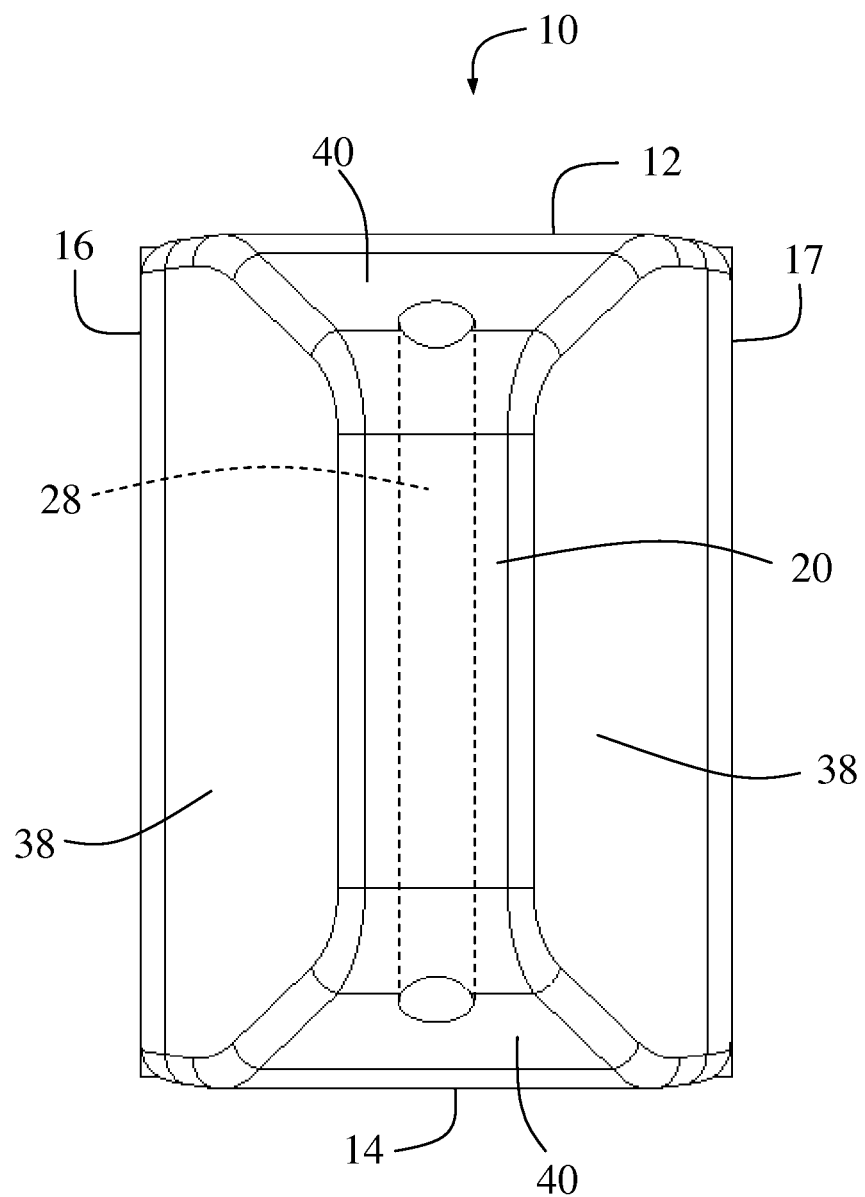
FIG. 7 is a plan view of a proximal end view of the spinal fusion implant of FIG. 2.

FIG. 7 illustrates the distal end 20 of the spinal fusion implant 10 of the present invention. The distal end 20, as best illustrated in FIGS. 1 & 2, has a conical (bullet-shaped) shape including a pair of first tapered (angled) surfaces 38 and a pair of second tapered (angled) surfaces 40. First tapered surfaces 38 extend between lateral surfaces 16, 17 and the distal end 20, and function to distract the vertebrae adjacent to the target intervertebral space during insertion of the spinal fusion implant 10. Second tapered surfaces 40 extend between top and bottom surfaces 12, 14 and the distal end 20, and function to maximize contact with the anterior portion of the cortical ring of each adjacent vertebral body. Furthermore, second tapered surfaces 40 provide for a better fit with the contour of the vertebral body endplates, allowing for a more anterior positioning of the spinal fusion implant 10 and thus advantageous utilization of the cortical rings of the vertebral bodies.

FIGS. 8-10 illustrate the spinal fusion implant 10, according to an example embodiment, in which the implant 10 has a variable height tapering in a direction oblique to the length and width of the implant, as measured by the distance between the top and bottom surfaces 12, 14.

Figure 14:
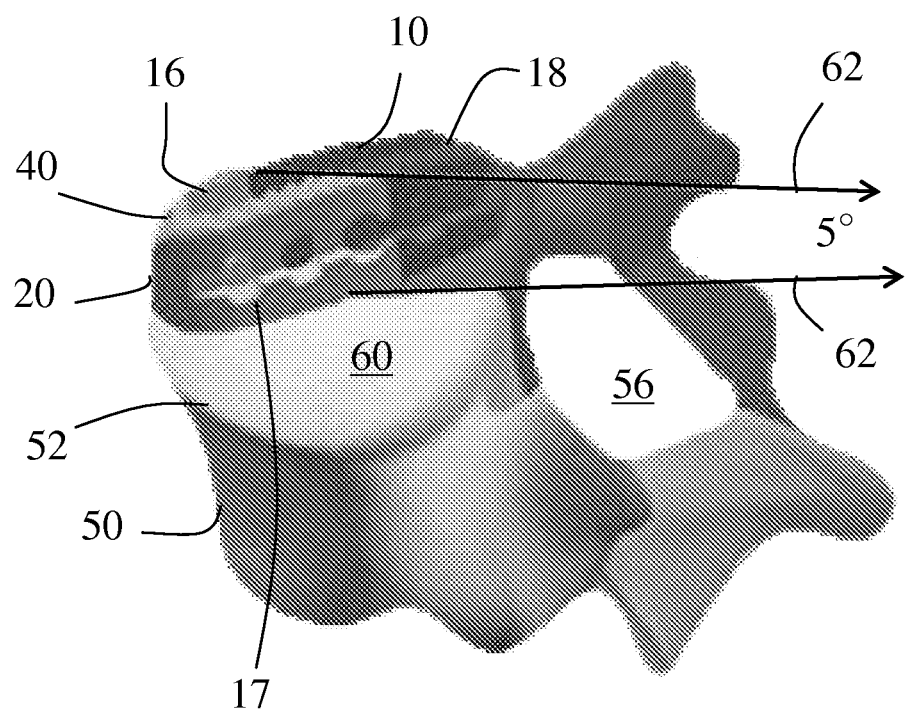
FIG. 14 is a perspective view of a spinal fusion implant of the present invention inserted into an intervertebral space in a unilateral oblique fashion

FIG. 8 is a perspective view highlighting the top surface 12 of the implant 10. Phantom arrows are used to indicate the general direction in which the height of the implant tapers from a larger height at the end of the arrows to a lesser height at the point of the arrows. Because the variable height of the implant tapers in a direction oblique to the length of the implant, the height of the implant at the distal end 20 is greater than the height of the proximal end 18. This is depicted in FIG. 9 wherein the height of the distal end is shown as $H_1$ and the height of the proximal end is shown as $H_2$. Because the direction in which the height of the implant tapers is also oblique to the width of the implant, the height of the first lateral side 16 differs from the height of the second lateral side 17 along at least a portion of the length of the implant. This is depicted in FIG. 10 wherein the height of the first lateral side 16 at given point along the length of the implant is shown as $H_3$, which is greater than the height $H_4$ of the second lateral side 17 at the same point along the length. The practical result of this tapering along a direction oblique to the length and width of the implant is that when the spinal fusion implant 10 is inserted obliquely within the disc space, as best depicted in FIG. 14, the effective height correction occurs generally parallel to the sagittal plane (i.e. anterior to posterior). This provides for optimal restoration of the natural lordotic curvature of the lumbar spine. By way of example only, the oblique tapering of the implant 10 height may occur at an angle measuring from 5 to 10 degrees. According to the embodiment pictured in FIG. 14, the oblique taper occurs at a 5 degree angle.

According to a broad aspect of the present invention, the spinal fusion implant 10 may be introduced into a spinal target site through use of any of a variety of suitable surgical instruments having the capability to engage the implant 10. The spinal fusion implant 10 is capable of being used in minimally invasive surgical procedures, needing only a relatively small operative corridor for insertion. By way of example only, the spinal fusion implant 10 will now be described in relation to a transforaminal lumbar interbody fusion (TLIF) technique, in which the intervertebral disc space is approached from a postero-lateral direction, however it should be understood that the spinal fusion implant 10 is capable of use in a variety of surgical procedures not described herein. After creation of this operative corridor and preparing the disc space (using techniques commonly known and used in the art), the spinal fusion implant 10 is mated to an insertion device (not shown) and advanced through the operative corridor toward the target intervertebral space. At this point the spinal fusion implant 10 is oriented with the lateral sides 16, 17 facing in a caudad/cephalad direction, for example with the first lateral side 16 facing a caudad (inferior) direction and the second lateral side 17 facing a cephalad (superior) direction. When the distal end 20 of the implant 10 reaches the intervertebral disc space, each of the pair of first tapered surfaces 38 will come into contact with one of the adjacent vertebral bodies. As the implant 10 is advanced into the intervertebral disc space, the pair of first tapered surfaces 38 will serve to distract the vertebral bodies, allowing the implant to fully enter the intervertebral space.

Since the first and second lateral sides 16, 17 are preferably provided with generally smooth surfaces, the spinal fusion implant 10 should advance with relative ease into the disc space once the adjacent vertebral bodies have been distracted. Once the implant 10 has been positioned in its desired location, the user will then rotate the implant 90° such that the top and bottom surfaces 12, 14 face in a caudad/cephalad direction and the anti-migration features 24 engage the vertebral bodies. Significantly, the direction of rotation is critical to ensure proper placement of the implant 10 such that the edges of the proximal surface 34 rest on the cortical ring of the vertebral bodies, that the proximal surface 34 does not protrude into the spinal canal, and if the implant includes a variable height, the implant tapers in the appropriate direction (e.g. anterior to posterior rather than posterior to anterior). For example, if the spinal fusion implant 10 approaches a patient's spine posteriorly from the right with the (longer) first lateral side 16 facing caudally, then implant 10 must be rotated in a counter-clockwise direction to achieve proper positioning. Similarly, if the spinal fusion implant 10 approaches a patient's spine posteriorly from the left side with the (longer) first lateral side 16 facing caudally, then implant 10 must be rotated in a clockwise direction to achieve proper positioning. According to one embodiment the implant may include one or more markings or other indicia to help facilitate the proper positioning. According to one embodiment (not shown), for example, the first lateral side 16 may be marked with "lateral" to indicate that it should face to the exterior of the disc space, and the second lateral side 17 may be marked with "Medial" to indicate that it should face the interior of the disc space when the implant 10 is rotated into position. Once the spinal fusion implant 10 has been rotated into position, the inserter may be detached and removed from the operative corridor.

Radiographic markers 26, 27, 28 may be utilized to aid in visual confirmation of proper placement of the spinal fusion implant 10. For example, when the implant 10 is properly positioned in the intervertebral space, radiographic markers 26, 27 (and others, if applicable) should be aligned such that the two (or more) markers 26, 27 positioned along the proximal end 18 appear as one when viewing a radiographic image of the spine from a lateral point of view. These markers should appear to be adjacent to the posterior portion of the cortical ring of the vertebral bodies. Likewise, the radiographic marker 28 at the distal end 20 should appear to be adjacent to the anterior portion of the cortical ring. If the proximal radiographic markers 26, 27 appear to be either misaligned or protruding into the spinal canal, or if any of the markers 26, 27, 28 appear otherwise misplaced, the surgeon may choose to reassess the placement of the implant 10. If the surgeon determines that the implant was not properly placed, then the implant 10 may be rotated in the opposite direction, repositioned, and rotated once more so that the top and bottom surfaces 12, 14 engage the vertebral bodies.

Figure 11:
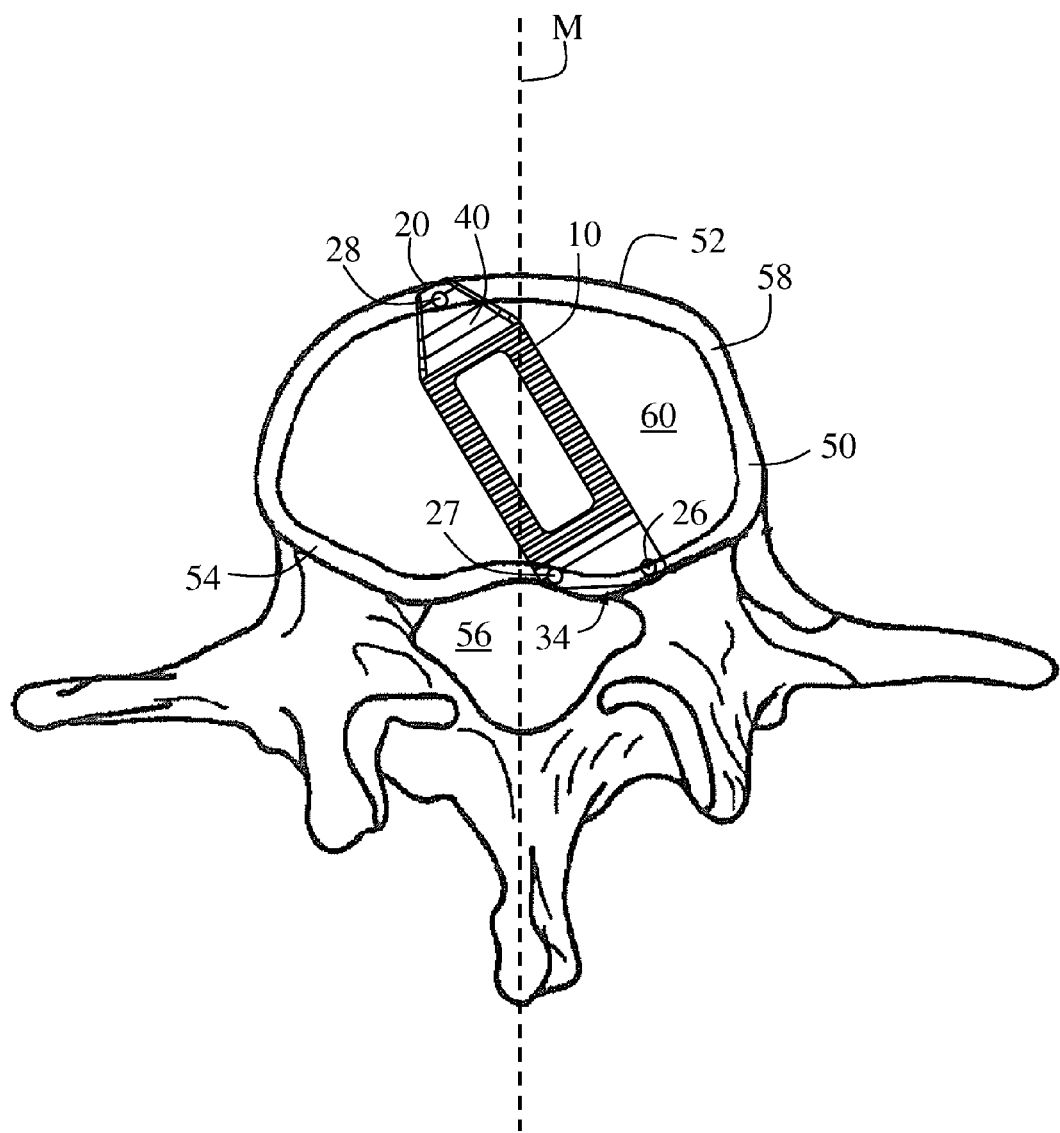
FIG. 11 is a top plan view of an example of a spinal fusion implant of the present invention inserted into an intervertebral space in a unilateral configuration.
Figure 12:
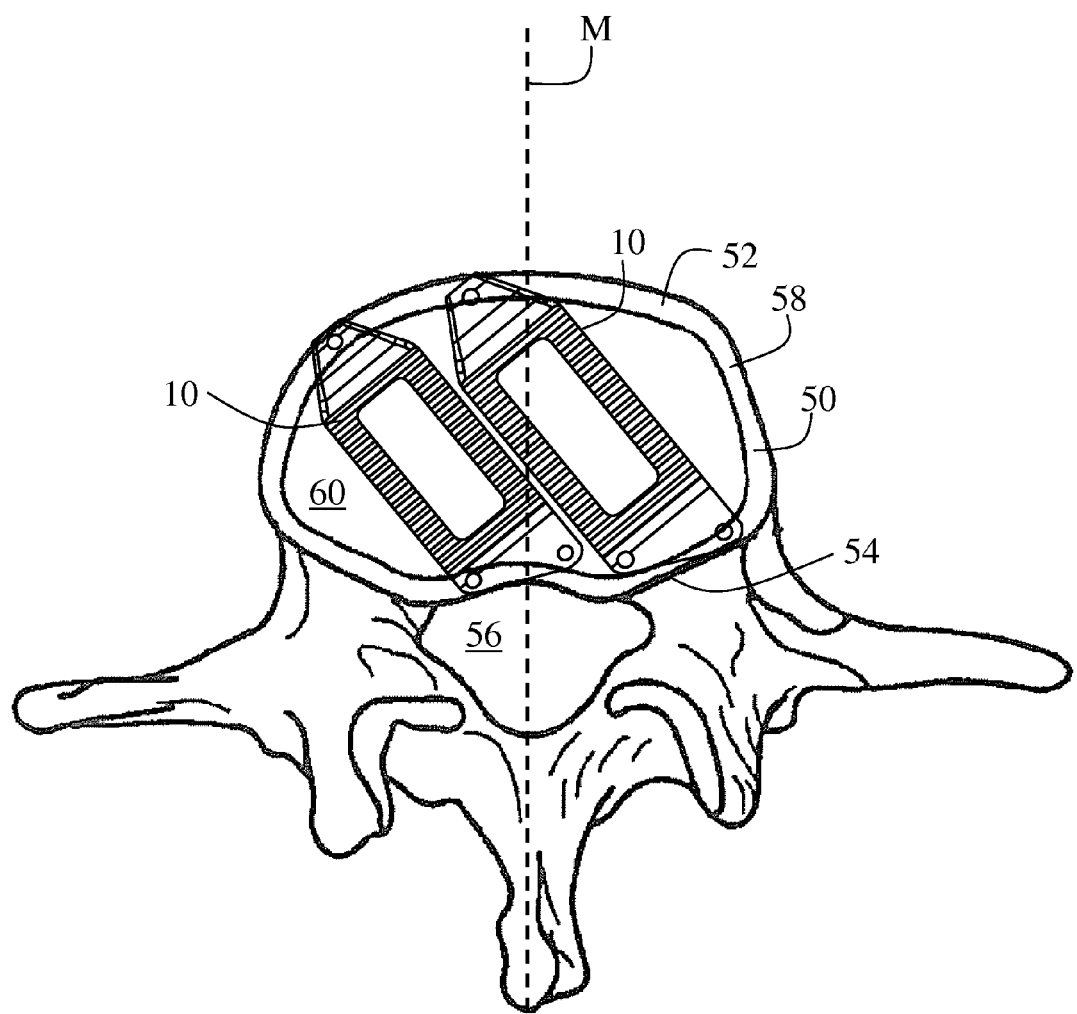
FIG. 12 is a top plan view of an example of a spinal fusion implant of the present invention inserted into an intervertebral space in a paired unilateral configuration.
Figure 13:
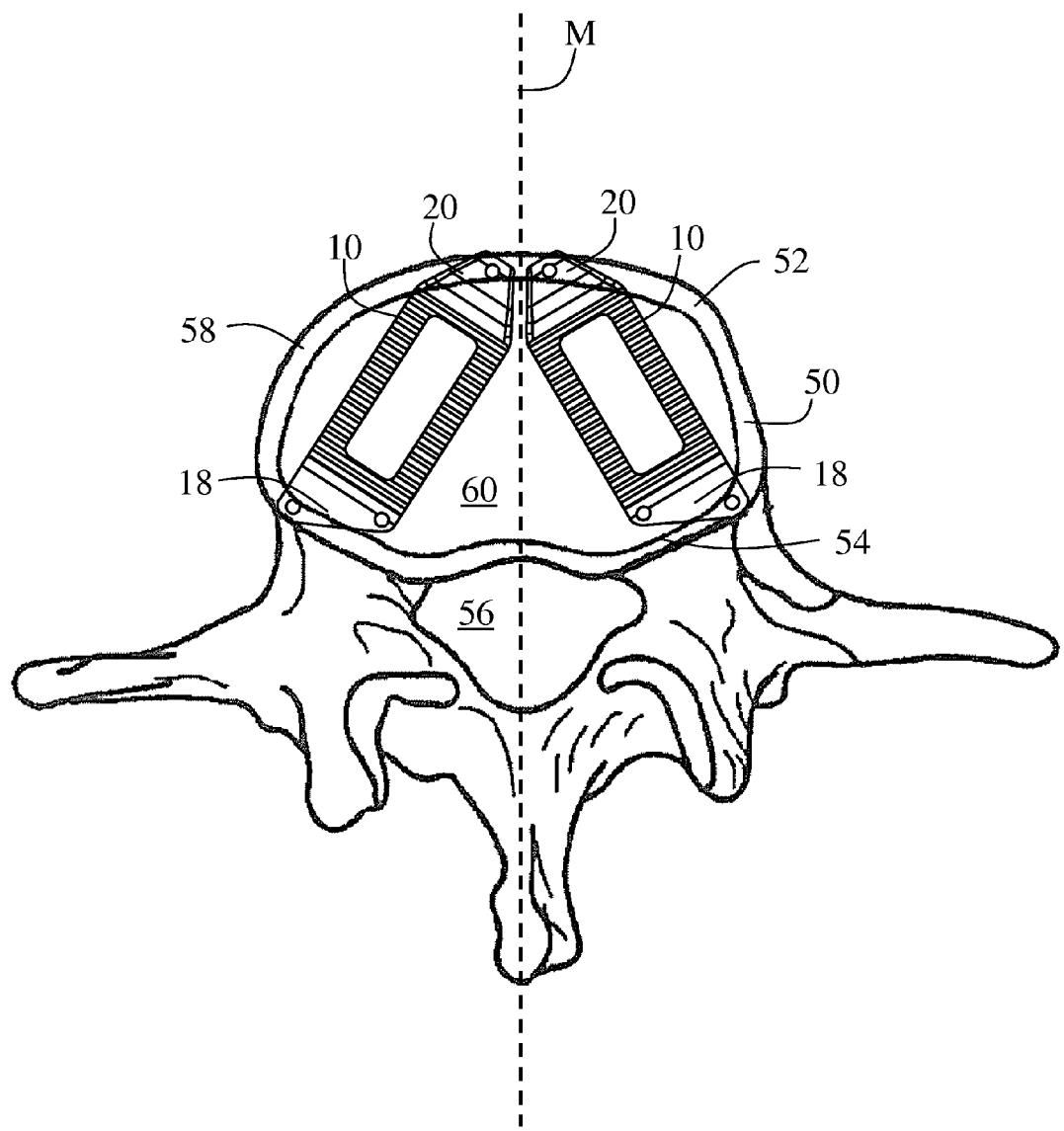
FIG. 13 is a top plan view of an example of a spinal fusion implant of the present invention inserted into an intervertebral space in a bilateral configuration.

Referring to FIGS. 11-13, one or more of the spinal fusion implant 10 of the present invention may be used in a variety of configurations in a fusion procedure, including but not limited to (and by way of example only) unilateral, paired unilateral and bilateral. For the purposes of the subsequent discussion, the intervertebral space is defined as a volume extending between adjacent vertebral bodies, having a perimeter shape that is determined by the perimeter shapes of the adjacent vertebral bodies. As shown by example in FIGS. 11-13, the intervertebral space further has a midline M defined by a line bisecting the intervertebral space in an anterior-posterior direction. Each vertebral body 50 (and consequently the intervertebral space) has a generously curved anterior portion 52 and a slightly curved (nearly planar) posterior portion 54. The posterior portions 54 of the vertebral bodies 50 and the intervertebral space lie adjacent to the spinal canal 56. Moreover, each vertebral body has a ring 58 made of stronger cortical bone surrounding an interior 60 made of cancellous bone.

Referring to FIG. 11, in a unilateral configuration a single implant 10 is inserted into an intervertebral disc space according to the procedure described above. Preferably, the implant 10 is positioned obliquely across the disc space with the implant 10 making advantageous use of the outer rings 58 of cortical bone in each of the adjacent vertebral bodies 50. The oblique positioning of the implant 10 includes positioning the implant 10 such that the distal end 20 is on one side of the midline of the intervertebral space and the proximal end 18 is on the other side of the midline. Preferably, as previously noted, when properly positioned the edge of the proximal surface 34 will interface with the cortical bone in the posterior portion 54 of the vertebral bodies 50. As a result, the proximal surface 34 will coincide with a portion of the posterior perimeter of the intervertebral space, and the implant 10 does not encroach upon the spinal canal 56. Furthermore, the distal end 20 is configured to interface with the cortical bone 58 in the anterior portion 52 of the vertebral bodies 50. The contour of each vertebral body 50 is such that the anterior portion 52 has a curvature amounting to a slightly raised lip to prevent the disc from slipping out of the space. This lip often causes problems with inserting an intervertebral implant completely within the space, and results in an inability of the implant to take advantage of the cortical bone rings 58 in the anterior portion of the disc space. Significantly, the spinal fusion implant 10 includes second tapered surfaces 40 extending between the top and bottom surfaces 12, 14 and the distal end 20. Second tapered surfaces 40 allow the distal end 40 to interface with the lip of the vertebral body 50 and therefore take full advantage of the strong cortical bone 58.

Referring to FIG. 12, in a paired unilateral configuration, a first spinal fusion implant 10 is inserted into the disc space according to the procedure described above, with one notable exception. In this configuration, the first spinal fusion implant 10 is not positioned directly across the midline M of the intervertebral space. In other words, the proximal end 18 and distal end 20 may or may not be on different sides of the midline M depending on the size and contour of the specific patient. However, the first implant 10 is still positioned obliquely within the intervertebral space such that the proximal surface 34 coincides with a proximal portion of the perimeter of the intervertebral space. Once the first implant 10 has been fully inserted (and rotated into position), a second spinal fusion implant 10 is inserted directly adjacent to the first implant 10. Upon final positioning and rotation, the second spinal fusion implant 10 should be oriented adjacent to the first spinal fusion implant 10 such that the implants 10 are in a side-by-side position.

Referring to FIG. 13, in a bilateral configuration, a first spinal fusion implant 10 is inserted into the disc space according to the procedure described above, except that the first implant 10 should be disposed entirely on one side of the midline M of the intervertebral space. Once the first implant 10 has been fully inserted (and rotated into position), a second spinal fusion implant 10 is inserted into the disc space from the minor-image postero-lateral approach. For example, if the first spinal fusion implant 10 is inserted postero-laterally from the right, then the second spinal fusion implant 10 should be inserted postero-laterally from the left. The fully inserted second spinal fusion implant 10 should occupy the portion of the intervertebral space on the opposite side of the midline from the first spinal fusion implant 10. As a result, when fully inserted the distal ends 20 of the implants 10 will be situated near each other in the anterior portion of the disc space on opposite sides of the midline M.

FIG. 14 illustrates a perspective view of the spinal fusion implant 10 positioned obliquely within the disc space as in FIG. 13, but wherein the implant 10 includes a variable height tapering along a direction oblique to the length and width of the implant. The vertebral body 50 is shown shaded in a darker color on one side of the midline and in a lighter color on the other side of the midline. The spinal fusion implant 10 is positioned obliquely across the midline and is shaded in similar fashion to the vertebral body 50 indicating the position of the implant 10 relative to the midline. The arrows 62 help illustrate the oblique taper angle of the implant 10 (shown, by way of example only, as 5 degrees) in addition to the direction of the taper oriented oblique to both the length and width of the implant. The combination of the oblique taper and the oblique implant positioning act to vary the height of the disc space in the sagittal (anterior-posterior) plane and restore the natural lordotic curvature of the spine.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A spinal fusion implant for insertion between first and second vertebral bodies, each vertebral body having a cancellous bone interior bounded by a cortical bone exterior wall, each vertebral body having a generously curved anterior portion and slightly curved posterior portion, said posterior portion adjacent to a spinal canal, said spinal fusion implant comprising:
   an article having opposing first and second engagement sides, a central aperture extending through said first and second engagement sides, opposing first and second lateral sides, a lateral channel disposed along each of said first and second lateral sides, a proximal end, an distal end, a width between said opposing first and second lateral sides, and a length between said proximal end and distal end, a first height between said opposing first and second engagement sides at said distal end and at said first lateral side, a second height between opposing first and second engagement sides at said distal end and at said second lateral side, a third height at said proximal end and said first lateral side and a fourth height at said proximal end and at said second lateral side, wherein at least one of said first and second engagement sides is tapered between said distal and proximal ends along a direction oblique to said implant length and oblique to said implant width such that said first height is greater than said second height, said second height is greater than said third height and said third height is greater than said fourth height, wherein said first and second lateral sides are generally planar and said first lateral side has a greater length than the second lateral side, and further wherein said central aperture spans at least half of distance of said length.

2. The spinal fusion implant of claim 1, wherein said distal end is adapted to extend between said cortical walls of said anterior portions of said first and second vertebral bodies.

3. The spinal fusion implant of claim 1, wherein at least one of said proximal and distal ends is provided with at least one radiographic marker.

4. The spinal fusion implant of claim 1, wherein at least one of said first and second engagement sides is provided with an anti-migration feature.

5. The spinal fusion implant of claim 4, wherein said anti-migration feature comprises a plurality of ridges.

6. The spinal fusion implant of claim 1, wherein said taper is measured at an angle of 5 degrees.

7. The spinal fusion implant of claim 1, wherein said first and second engagement sides are at least one of generally planar, generally convex and generally concave.

8. The spinal fusion implant of claim 1, further comprising at least one lateral aperture extending through said implant between said first and second lateral sides.

9. The spinal fusion implant of claim 1, wherein said distal end comprises a first tapered surface extending between said distal end and said first lateral side and a second tapered surface extending between said distal end and said second lateral side.

10. The spinal fusion implant of claim 9, wherein said distal end comprises a third tapered surface extending between said distal end and said first engagement side and a fourth tapered surface extending between said distal end and said second engagement side.

11. The spinal fusion implant of claim 1, wherein said implant is made of at least one of poly-ether-ether-ketone, poly-ether-ketone-ketone, ceramic, metal and any combination of poly-ether-ether-ether-ketone, poly-ether-ketone-ketone, ceramic and metal.

* * * * *